(12) United States Patent
Mosbach et al.

(10) Patent No.: US 6,255,461 B1
(45) Date of Patent: *Jul. 3, 2001

(54) ARTIFICIAL ANTIBODIES TO CORTICOSTEROIDS PREPARED BY MOLECULAR IMPRINTING

(76) Inventors: Klaus Mosbach, Lackalaenga 31, S-244 94, Furulund (SE); Olof Ramstrom, Kallarekroken 64, S-226 37, Lund (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/628,381

(22) Filed: Apr. 5, 1996

(51) Int. Cl.$^7$ .............................. C07K 16/26; C08J 3/09
(52) U.S. Cl. .................................. 530/389.2; 264/331.18
(58) Field of Search ...................... 530/389.2; 264/330, 264/331.18

(56) References Cited

U.S. PATENT DOCUMENTS 5,630,978 * 5/1997 Domb .................................. 264/330
5,804,563 * 9/1998 Still et al. ............................. 514/26

FOREIGN PATENT DOCUMENTS

94/11403 * 5/1994 (WO).
WO 94/11403  5/1994 (WO).
WO 94/14835  7/1994 (WO).
WO 94/26381  11/1994 (WO).

OTHER PUBLICATIONS

B. Sellergren et al, J. Am. Chem. Soc., vol. 110, pp. 5853–5860. Highly Enantioselective and Substrate–Selective Polymers Obtained by Molecular Imprinting Utilizing Noncovalent Interactions, 1988.*
H. Dugas, *Bioorganic Chemistry*. A Chemical Approach to Enzyme Action, 1989. Table of Contents Only.
G. Wulff, *Molecular Imprinting In Cross–Linked Materials with the Aid of Molecular Templates–A Way towards Artificial Antibodies*, Agnew. Chem. Int. Ed. Engl., 1995, vol. 34, pp. 1812–1832.
O. Ramstrom, et al., *Chiral Recognition In Adrenergeric Receptor Binding Mimics Prepared By Molecular Imprinting*, J. Mol. Recogn., vol. 9, 691–696 (1996).
L.S. Goodman, et al., *The Pharmacological Basis of Therapeutics*, Pergamon Press, Inc. 1990 8th Ed. Table of Contents Only.
L.A. Kaplan, et al., *Clinical Chemistry: theory, analysis and correlation*, C.V. Mosby Co., 1984. Table of Contents Only.
Lewis, J. G., Manley, L. Whitlow, J.C. & Elder, P.A. 1992. *Production of monoclonal antibody to cortisol: application to a direct enzyme–linked immunosorbent assay of plasma*. Steroids, 1992, vol. 57 Feb., pp. 82–85.
Diane R. Smith; "Supramolecular Chemistry"; *Chemistry & Industry*; Jan. 1994; No. 1, pp. 1–40.

Shashi Mahato, et al.; "Steroid Transformations By Microorganisms–III"; *Phytochemistry*; 1989; vol. 28, No. 1, pp. 7–40.
Kenneth J. Shea; "Molecular Imprinting of Synthetic Network Polymers: The De Novo Synthesis of Macromolecular Binding and Catalytic Sites"; *TRIP*; May 1994; vol. 2, No. 5, pp. 166–173.
Dario Kriz, et al.; "Introducing Biomimetic Sensors Based on Molecularly Imprinted Polymers as Recognition Elements"; *Anal. Chem.*; 1995; vol. 67, pp. 2142–2144.
Ian A. Nicholls; "Thermodynamic Considertions for the Design of and Ligand Recognition by Molecularly Imprinted Polymers"; *Chemistry Letters*; Nov. 1995; No. 11, pp. 1035–1036.
Ralf Müller, et al.; "Molecularly Imprinted Polymers Facilitating a β–Elimination Reaction"; *Makromol. Chem., Rapid Commun.*; 1993; vol. 14, No. 10, pp. 637–641.
George Vlatakis, et al.; "Drug Assay Using Antibody Mimics Made by Molecular Imprinting"; *Letters to Nature*; Feb. 1993; vol. 361, pp. 645–647.
E. Styrbjörn Byström, et al.; "Selective Reduction of Steroid 3– and 17–Ketones Using LiAlH$_4$ Activated Template Polymers"; *J. Am. Chem. Soc.*; 1993; vol. 115, pp. 2081–2083.
Lutz Fischer, et al.; "Direct Enantioseparation of β–Adrenergic Blockers Using a Chiral Stationary Phase Prepared by Molecular Imprinting"; *J. Am. Chem. Soc.*; 1991; vol. 113, pp. 9358–9360.
John G. Lewis, et al.; "Production of a Monoclonal Antibody to Cortisol: Application to a Direct Enzyme–Linked Immunosorbent Assay of Plasma"; *Steroids*; 1992; vol. 57, pp. 82–85.
Olaf Ramström, et al.; "Recognition Sites Incorporating Both Pyridinyl and Carboxy Functionalities Prepared by Molecular Imprinting"; *J. Org. Chem.*; 1993; vol. 58, pp. 7562–7564.
Olof Ramström, et al.; "Synthetic Peptide Receptor Mimics: Highly Stereoselective Recognition in Non–Covalent Molecularly Imprinted Polymers"; *Tetrahedron: Asymmetry*; Apr., 1994; vol. 5, No. 4, pp. 649–656.
Eeva–Liisa Sainio, et al.; "Radioimmunoassay of Total and Free Corticosterone in Rat Plasma: Measurement of the Effect of Different Doses of Corticosterone"; *Steroids*; May–Jun. 1988; vol. 51, Nos. 5–6; pp. 609–623.
Lars I. Andersson; "Application of Molecular Imprinting to the Development of Aqueous Buffer and Organic Solvent Based Radioligand Binding Assays for (S)–Propranolol"; *Anal. Chem.*; 1996; vol. 68, pp. 111–117.

(List continued on next page.)

Primary Examiner—Mary E. Ceperley
(74) Attorney, Agent, or Firm—Morgan & Finnegan, LLP (57) ABSTRACT

The invention relates to artificial antibodies that are prepared by molecular imprinting, where methacrylic acid, ethylene glycol dimethacrylate and a print molecule are combined to form an artificial antibody having spatially positioned binding sites dictated by the corticosteroid print molecule, and the antibodies can be used in separation and analytical procedures.

10 Claims, 5 Drawing Sheets

OTHER PUBLICATIONS

Lars I. Andersson, et al.; "Mimics of the Binding Sites of Opioid Receptors Obtained by Molecular Imprinting of Enkephalin and Morphine"; *Proc. Natl. Acad. Sci. USA*; May, 1995; vol. 92, pp. 4788–4792.

William P. Jencks; "On the Attribution and Additivity of Binding Energies"; *Proc. Natl. Acad. Sci. USA*; Jul. 1981; vol. 78, pp. 4046–4050.

Kurt Nilsson, et al.; "Imprinted Polymers as Antibody Mimetics and New Affinity Gels for Selective Separations in Capillary Electrophoresis"; *J. Chromatogr.*; 1994; vol. 680, pp. 57–61.

Maria Kempe, et al.; "Direct Resolution of Naproxen on a Non–Covalently Molecularly Imprinted Chiral Stationary Phase"; *J. Chromatogr.*; Apr., 1994; vol. 664, No. 2, pp. 276–279.

James Beach, et al.; "Designed Catalysts. A Synthetic Network Polymer That Catalyzes the Dehydrofluorination of 4–Fluoro–4–(p–Nitrophenyl)Butan–2–One"; *J. Am. Chem. Soc.*; Jan., 1994; vol. 116, No. 1; pp. 379–380.

Michael Whitcombe, et al.; "A New Method for the Introduction of Recognition Site Functionality into Polymers Prepared by Molecular Imprinting: Synthesis and Characterization of Polymeric Receptors for Cholesterol"; *J. Am. Chem. Soc.*; Jul. 1995; vol. 117, pp. 7105–7111.

R.W. Purchas, et al.; "A Simple Method for Separating Unbound and Bound Cortisol in a Radioimmunoassay"; *Anal. Biochem.*; Sep., 1985, vol. 149, pp. 399–403.

Klaus Mosbach, et al.; "Preparation and Application of Polymer–Entrapped Enzymes and Microorganisms in Microbial Transformation Processes with Special Reference to Steroid 11–β–Hydroxylation and $\Delta^1$–Dehydrogenation"; *Biotech. Bioeng.*; Jan. 1970; vol. 12, pp. 19–27.

Sundaresan Vidyasankar, et al.; "Molecular Imprinting: Selective Materials for Separations, Sensors and Catalysis"; *Curr. Opin. Biotechnol.*; 1995; vol. 6, No. 2, pp. 218–224.

Richard Ansell, et al.; "Molecularly Imprinted Polymers for Bioanalysis: Chromatography, Binding Assays and Biomimetic Sensors"; *Curr. Opin. Biotechnol.*; Feb. 1996; vol. 7, No. 1, pp. 89–94.

Klaus Mosbach, et al.; "The Emerging Technique of Molecular Imprinting and Its Future Impact on Biotechnology"; *Biotechnology.*; Feb. 1996; vol. 14, pp. 163–170.

* cited by examiner

Cortisol

FIG. 3

Cortisone

FIG. 4

21-Deoxycortisol

FIG. 5

Corticosterone

FIG. 6

11-Deoxycortisol

FIG. 7

Prednisolone

ARTIFICIAL ANTIBODIES TO CORTICOSTEROIDS PREPARED BY MOLECULAR IMPRINTING

FIELD OF THE INVENTION

The present invention relates to artificial antibodies that selectively recognize steroids and act as antibody and receptor binding mimics. More specifically, the present invention relates to molecularly imprinted polymers (MIPs) that selectively recognize cortisol and corticosterone based steroids, their preparation and use in analyses, therapies and separation procedures.

BACKGROUND OF THE INVENTION

Molecular imprinting is a technique devised to generate a polymeric material that is analyte specific. The analyte can be any organic molecule, biological or macromolecule. Molecular imprinting has been used to prepare materials that recognize proteins or other biological compounds, especially where the structural information needed for rational design is lacking. Likewise, if a natural receptor is poorly characterized or difficult to isolate, artificially prepared mimics may serve as a useful alternative. Furthermore, such polymers are considerably less costly to produce when compared to, e.g., antibodies and receptors.

Antibodies are used in several areas, such as therapy, immunoaffinity and purification. Of particular interest is the use of antibodies in immunoassays. However, antibodies for these procedures are normally produced by immunizing animals with the corresponding antigen leading to polyclonal antibodies, or by using fused cells (B cells) allowing the obtained cell lines to produce monoclonal antibodies.

As an alternative, some non-biologically derived antibody mimics or artificial antibodies have been described. For example, the anti-theophylline and anti-diazepam polymers, i.e., mimics, prepared in accordance with the teachings of PCT Application WO 94/11403, the entirety of which is incorporated herein by reference. Such polymer structures are similar to biological antibodies in binding and recognizing antigens and avoid the need for animal sources. These antibody mimics are especially useful where it is difficult or impossible to raise antibodies.

The object of creating artificial counterparts to natural macromolecular binding entities, such as proteins, is of great interest. Employing natural macromolecules in rough environments such as high temperatures and pressures (e.g., sterilization conditions) is of major concern for many applications because of their natural sensitive properties. Furthermore, the efficiency and selectivity exerted by, e.g., receptors interacting with agonists and antagonists or antibodies recognizing antigens, is difficult to reproduce in synthetic systems [1]. Molecular imprinting provides an alternative to other approaches such as sophisticated procedures used in the field of supramolecular chemistry [2].

The rapidly mushrooming field of molecular imprinting is derived from the concept of creating designed recognition sites in macromolecular matrices by means of template polymerization [3–7]. Molecularly imprinted polymers have been shown to possess remarkable recognition properties that have been used in various fields such as drug separations [8–10], receptor mimics [11–14], bio-mimetic sensors [15], antibody mimics [16], template-assisted synthesis [17] and catalysis [18–19].

Of particular interest are the corticosteroids produced in the adrenal cortex and possess numerous and wide-spread effects in vivo. For example, the corticosteroids influence (1) metabolism, (2) electrolyte and water balance, (3) anti-inflammatory action, and (4) functions of the nervous system [20]. Many medical analyses where corticosteroids are of concern, e.g., in the assessment of the functional status of the adrenal cortex, utilize antibody-based assay methods such as RIA and ELISA for the selective recognition of a desired corticosteroid [21]. However, in addition to the general biological interest of steroid interactions with, e.g., antibodies and receptors, these substances are potentially useful for the study of molecular recognition phenomena [22]. The rigid structure of the fused ring system leads to a minimized number of conformations that the molecules may adopt in the interactions with recognition matrices resulting in higher binding strength since the entropy loss in binding is smaller [23] and a multitude of structurally very closely resembling structures are available. However, the limited number of polar interacting points necessary for non-covalent interactions inevitably leads to a decreased binding performance, and molecularly imprinted polymers against steroids have previously only been acquired using strong covalent binding systems such as carboxylic esters and carbonic acid esters [17,24].

Thus, a need exists for molecularly imprinted polymers (MIPs) that selectively recognizing steroid structures, steroid hormones, and in particular, steroids such as cortisol and corticosterone based steroids.

SUMMARY OF THE INVENTION

The present invention relates to molecular imprinting as a tool for making polymers that mimic anti-corticosteroid antibody binding, the artificial antibodies, their preparation and use. Molecularly imprinted polymers were prepared against cortisol and corticosterone compounds and the ligand specificity was assayed using a radioimmunoassay technique. The binding characteristics of the cortisol and corticosterone imprinted polymers were estimated and equilibrium constants were determined.

An object of the present invention is to provide an artificial antibody, formed from polymerizable monomers, containing preset binding sites for a hormone steroid compound or derivative.

Another object of the present invention is to provide an artificial antibody, formed from polymerizable monomers, containing preset binding sites for a corticosteroid compound or derivative.

Another object of the present invention is to provide a process for preparing an artificial antibody, formed from polymerizable monomers, containing preset binding sites for a corticosteroid compound or derivative, i.e., print molecule.

A still further object is to provide a process where the polymerization of functional monomers is carried out in the presence of a porogenic solvent and, a corticosteroid print molecule which is non-covalently bound to the functional groups of the monomer and/or copolymer. Subsequent removal of the print molecule from the rigid polymer results in sites within the polymer that are complementary to and have an affinity for the original print molecule. The sites provide a preset or predetermined spatial orientation of the polymer's functional groups to selectively separate a molecule or compound of interest.

A still further object of the present invention is to provide a process for separating steroids by using the antibody mimics according to the present invention.

Another object of the present invention is the use of the corticosteroid selective mimics in immuno and radioimmunoassay procedures.

A further object of the present invention is the use of artificial antibodies (corticosteroid selective mimics) in therapies and/or diagnoses, in which artificial antibodies are administrated to a mammal body, which artificial antibodies consist of a biocompatible polymer carrying specific binding sites mimicking the properties of antibodies towards an organic molecule.

These and other objects and advantages will become more apparent when considered with the following detailed description, non-limiting examples and drawings.

DETAILED DESCRIPTION OF THE INVENTION

In the present invention molecularly imprinted polymers were prepared against cortisol and corticosterone compounds. The polymers are prepared from the copolymerization of a monomer that is negatively charged, such as methacrylic acid (MAA) $CH_2=C(CH_3)COOH$ or itaconic acid with cross-linking ethylene glycol dimethacrylate monomer, with azo-bisisobutyronitrile as the initiator and were obtained from Merck (Darmstadt, FRG). Other negatively charged monomers include, but are not limited to acrylic acid, maleic acid, vinylbenzoic acid and 2-trifluoromethyl acrylic acid. Although the preferred cross-linking monomer is ethylene glycol dimethacrylate, other cross-linking monomers may be used, such as, divinylbenzene and trimethylolpropane trimethacrylate (TRIM). Scintillation liquid, Ecoscint O, was from National Diagnostics (Manville, N.J., USA). All solvents were of either HPLC or analytical grade.

The cortisol and corticosterone compounds include, but are not limited to cortisol, deoxycortisol, 11-deoxycortisol, 21-deoxycortisol, corticosterone, 21-deoxycortisone, 11-dehydrocorticosterone, cortexolone, prednisolone, substituted prednisolone and cortisone. Cortisol, corticosterone, 21-deoxycortisone, cortexolone, prednisolone and cortisone were obtained from Signa Chemical Co. (St. Louis, Mo., USA). [1,2,6,7-$^3$H]cortisol (specific activity 2.22 TBq/mmol) and (1,2,6,7-$^3$H]corticosterone (specific activity 3.03 TBq/mmol) were from Amersham International plc. (Little Chalfont, UK). In addition to the corticosteroids identified above, print molecules based on other steroid hormones, such as the androgens, estrogens, progestins, and gonadotropin releasing hormones identified in Basic and clinical Pharmacology, 4th Ed., 1989, pg. 696–700, incorporated herein by reference, may be used.

Ligand specificity was assayed using a radioimmunoassay technique and the binding characteristics of the cortisol and corticosterone imprinted polymers were estimated and equilibrium constants were determined.

The self-assembly imprinting protocol used in the present invention, where only non-covalent interactions are utilized in the formation and maintenance of the complexes between the functionally-active monomers and the print species, relies, to a large extent, upon the solvent that is used. In the present invention, more polar solvents had to be used due to the low solubility of the print species in non-polar solvents that are conventionally used for increasing the selectivity of the artificial recognition sites. Such conventional solvents include dichloromethane and toluene. The preferred polar solvents of the present invention include two different porogens, tetrahydrofuran and acetone. Other solvents may be used so long as they solubilize the steroid of interest and have the requisite polarity and could include chloroform, ethylacetate, isopropanol and acetonitrile.

The concentrations of the print species (molecules or compounds) in the protocols used was too high for reaching full solubility and were modified. Addition of functional monomer, i.e., methacrylic acid, to adjust the ratio to preferably about 10:1 (functional monomer to print molecule) provided clear solutions. The clear solutions indicated the establishment of strong interactions between the functional monomer and the print molecule (species).

The molecularly imprinted polymers (MIPs) were prepared according to Table 1 below.

TABLE 1

| Polymer | Print Molecule | Monomers (Ratio[a]) | Porogen |
|---|---|---|---|
| MIP1 | cortisol | MAA/EDMA(10:50) | tetrahydrofuran |
| MIP2 | cortisol | MAA/EDMA(10:50) | acetone |
| MIP3 | cortico-sterone | MAA/EDMA(10:50) | tetrahydrofuran |
| REF1 | none | MAA/EDMA | tetrahydrofuran |
| REF2 | none | MAA/EDMA | acetone |

[a]Molar ratio relative to print molecule

The print molecule was dissolved in dry porogen, either tetrahydrofuran or acetone, together with the functional monomer, methacrylic acid. The cross-linking monomer, ethylene glycol dimethacrylate, and the initiating agent, azo-bisisobutyronitrile, were added and the solutions were chilled on an ice-bath and purged thoroughly with nitrogen for ten minutes. The degassed solution was photolytically polymerized under nitrogen atmosphere at 4° C. overnight by use of a standard laboratory UV-source at 366 nm (CAMAG, Bubendorf, CH). The resulting polymer was crushed, ground in a mechanical mortar (Retsch, Haan, FRG) and wet-sieved (25: μm, Retsch) with water. Fine particles were removed through repeated sedimentation in acetone. The print species were extracted by extensive washing with a methanol/acetic acid solution (9:1, v/v), followed spectrophotometrically at 242 nm until no more print molecule could be detected.

Figure 1:
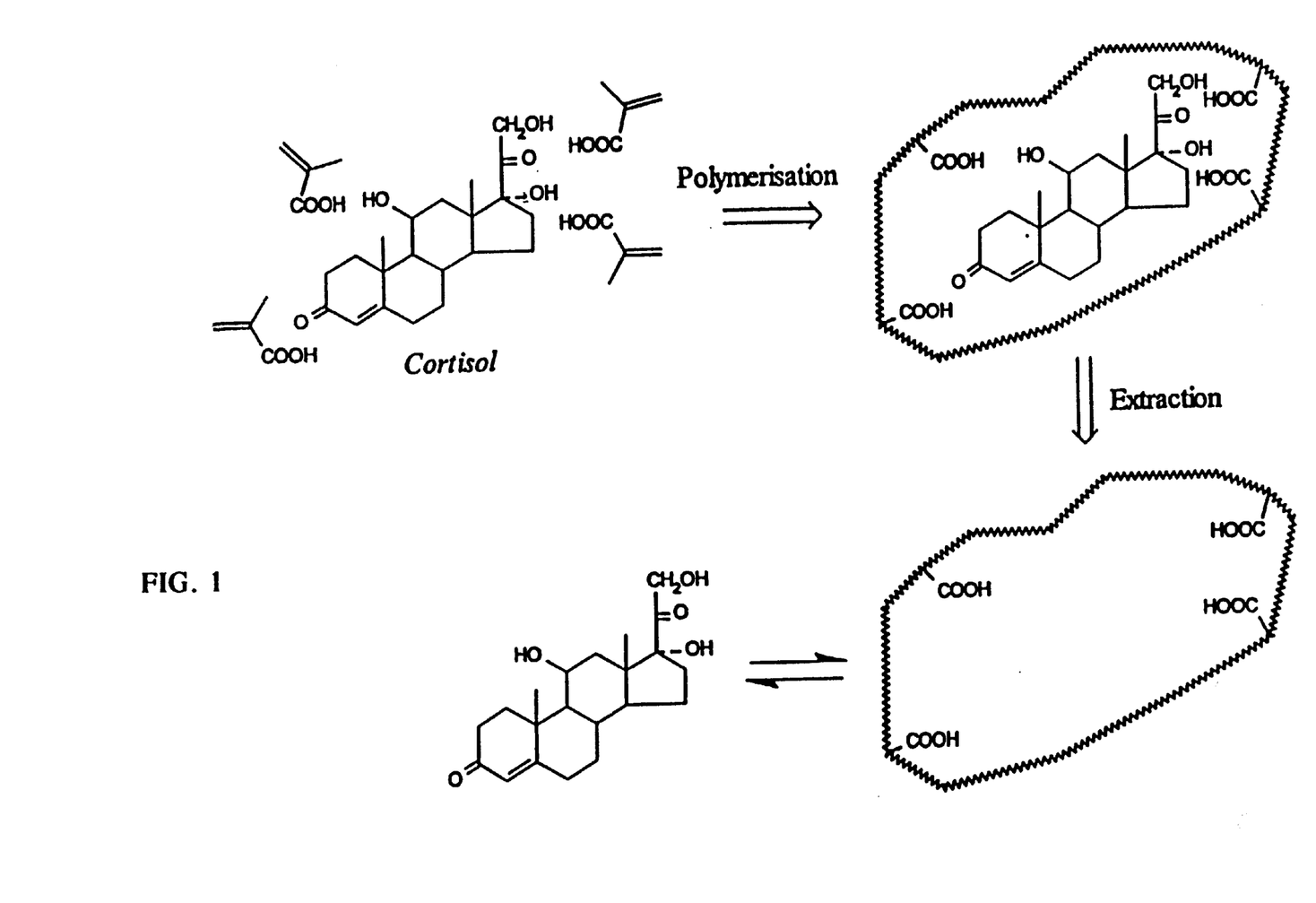
FIG. 1 shows a schematic of the molecular imprinting procedure according to the present invention.
Figure 2:
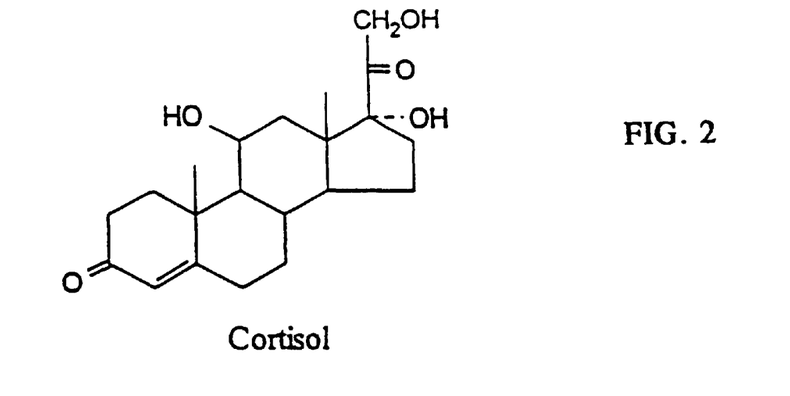
FIG. 2 shows the chemical structure of the cortisol (hydrocortisone) print molecule.
Figure 3:
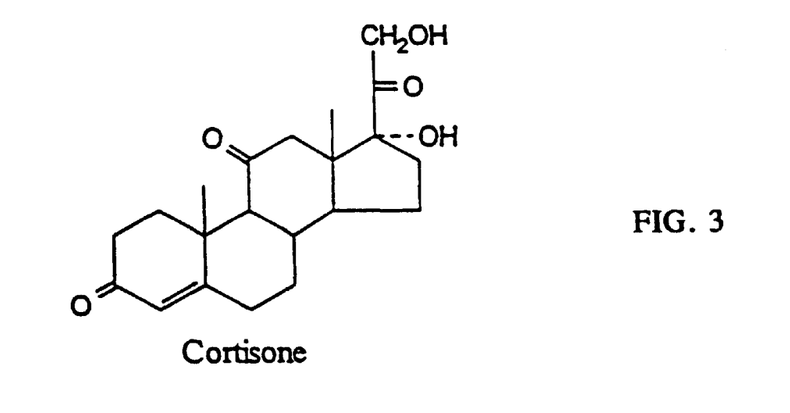
FIG. 3 shows the chemical structures of the cortisone print molecule.
Figure 4:
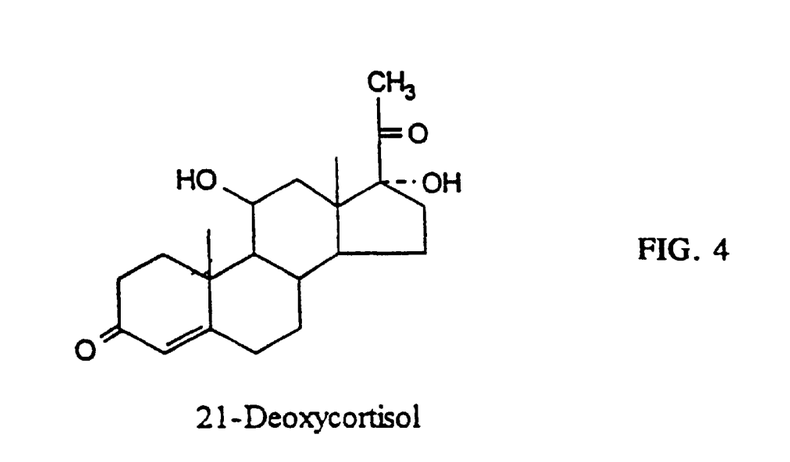
FIG. 4 shows the chemical structure of 21-deoxycortisol molecule.
Figure 5:
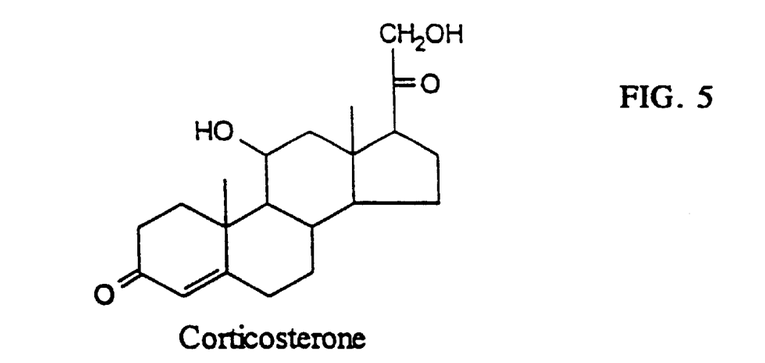
FIG. 5 shows the chemical structure of corticosterone print molecule.
Figure 6:
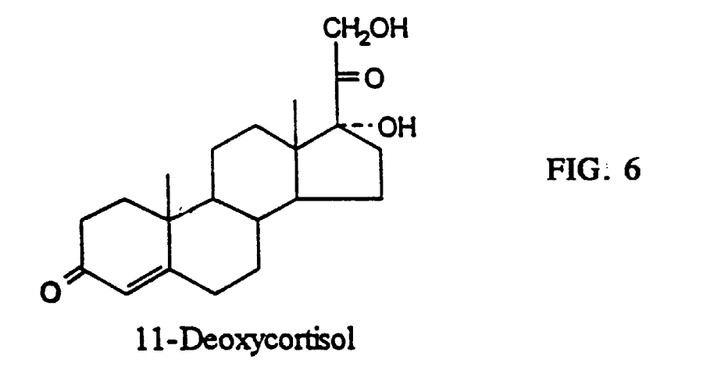
FIG. 6 shows the chemical structure of 11-deoxycortisol print molecule.
Figure 7:
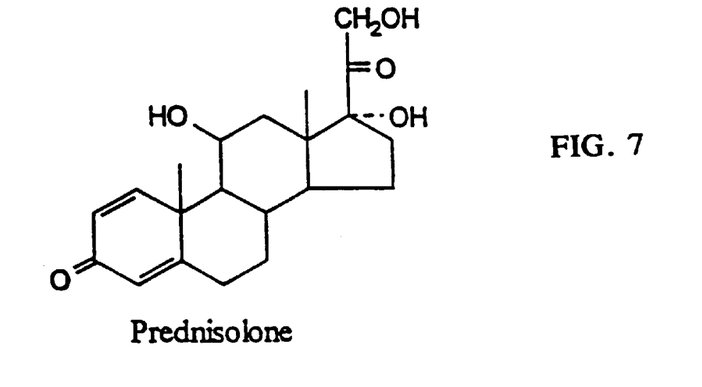
FIG. 7 shows the chemical structure of the prednisolone print molecule.

As shown in FIG. 1, the print molecule (cortisol) is initially dissolved in the porogen (tetrahydrofuran or acetone) and allowed to form non-covalent complexes to the functional monomer (methacrylic acid). Following addition of cross-linker (ethylene glycol dimethacrylate) and initiator (azo-bisisobutryonitrile), these complexes are arrested by polymerization. Finally, the print molecule is extracted by washing and the molecularly imprinted polymer is ready for association/dissociation studies. A procedure similar to that shown in FIG. 1 is followed for the compounds of FIG. 3—cortisone; FIG. 4—21-deoxycortisol; FIG. 5—corticosterone; FIG. 6—11-deoxycortisol; and FIG. 7—prednisolone.

The capacity of the methacrylic acid/ethylene diglycol dimethacrylate (MAA/EGDA) polymers was measured by saturation studies. Radiolabelled ligand to an activity of 500 Bq was added to polymer particles ranging from a concentration of 0.03 to 20 mg/mL in a total volume of 1.0 mL solvent in polypropylene micro-centrifuge tubes (Brand, Wertheim, FRG). The binding was allowed to reach equilibrium at ambient temperature on a rocking table overnight. Subsequently, the polymer particles were removed from the samples by centrifugation at 10,000 g for five minutes and 500 μL of the supernatant was added to 10 mL of scintillation cocktail in 20 mL scintillation vials (National Diagnostics, Atlanta, Ga., USA) and the radioactivity was measured using a model 2119 RACKBETA β-radiation counter (LKB Wallac, Solentuna, Sweden).

The competition assays were performed in a similar way. Non-radiolabelled (cold) ligand ranging from 0.01 to 250 μg was mixed with 1.0 mg of polymer particles in polypropylene microcentrifuge tubes. Radiolabelled (hot) ligand to an activity of 500 Bq was added and the volume was made up to 1.0 mL with solvent. The samples were allowed to reach equilibrium overnight at ambient temperature on a rocking table. The amount of bound ligand was estimated after centrifugation at 10,000 g for five minutes and measuring the radioactivity of 500 μL supernatant by addition of the latter to 10 mL of scintillation liquid and measuring the radioactivity using a β-radiation counter. The concentration of ligand capable of displacing 50% of bound ligand ($IC_{50}$) was calculated using the computer software package EBDA/ LIGAND (Elsevier-Biosoft, Amsterdam, NL).

The capacities of the molecularly imprinted polymers for the print species were investigated by saturation of the polymer with increasing amount of ligand. The assays were performed in several different solvents, but optimal binding performance were achieved with mixtures of tetrahydrofuran and n-heptane. In order to achieve a higher solubility of the ligands for further studies, a small amount of acetic acid was added to the solvent. The resulting imprinting performance, as measured by the saturation studies, revealed no difference between the imprinting porogens, tetrahydrofuran or acetone, but tetrahydrofuran was chosen as the best porogen because of a closer resemblance with the solvent used in the analysis system. The amount of polymer capable of binding 50% of added radiolabelled print species was similar in the imprinted polymers, -1.4 mg in the anti-cortisol polymers (MIP1 and MIP2) and 2.0 mg in the anti-corticosterone polymer (MIP3). The corresponding values for the reference polymer (REF1) were 6.3 mg and 7.0 mg, respectively. Using a polymer concentration of 1 mg/mL, the bindings by the blank polymers were 10–16% of the binding by the imprinted polymers and this concentration level was chosen for further experiments.

Figure 8:
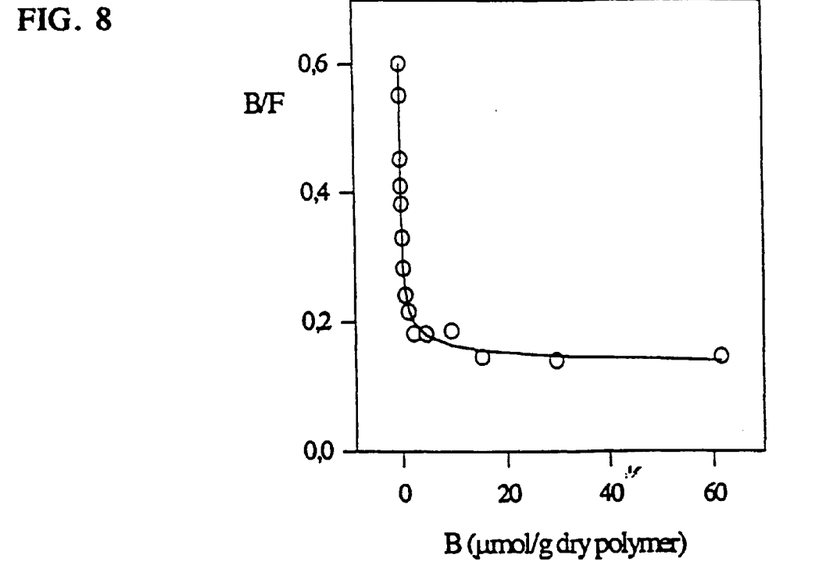
FIG. 8 shows the Scatchard plot for print species binding to imprinted polymers, i.e., cortisol binding by anti-cortisol polymer (MIP1), where B denotes the amount of bound ligand and F the amount of free ligand.
Figure 9:
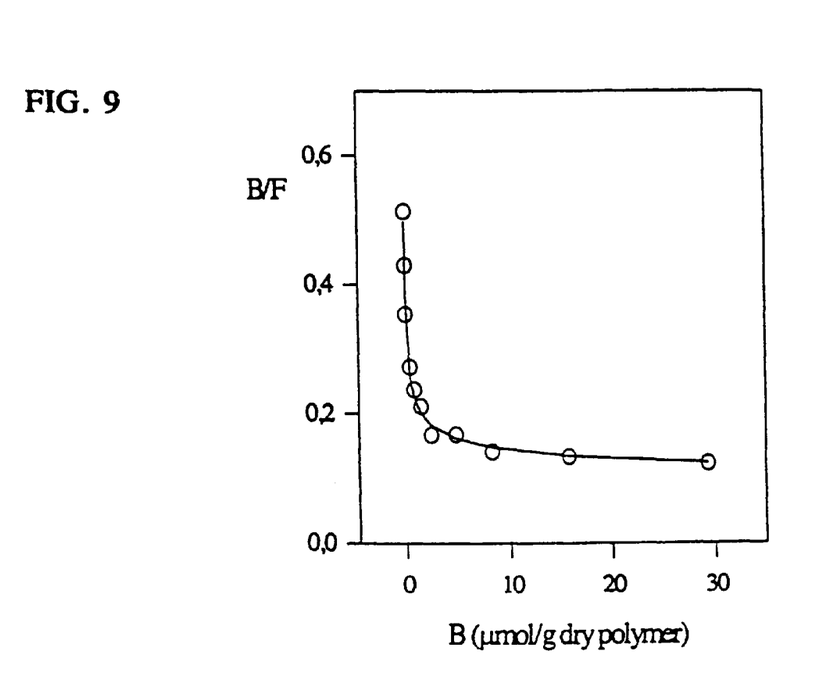
FIG. 9 shows the Scatchard plot for print species binding to imprinted polymers, i.e., corticosterone binding by anti-corticosterone binding by anti-corticosterone polymer (MIP3), where B denotes the amount of bound ligand and F the amount of free ligand.

The binding characteristics of the polymers are heterogeneous in nature, as reflected by the non-linear Scatchard plots shown in FIGS. 8 and 9. This "polyclonal" behavior is an unavoidable effect from the imprinting procedure, in which the weak, non-covalent, interactions between the template molecules and the functional monomers lead to the formation of gradually differing sites in the finished polymer. Thus, sites are formed of which the binding strength ranges from reasonably high affinity, exerted by a small amount of binding sites, down to larger number of sites with low affinity. Of the polymers studied, a two-site model can be readily employed to describe the binding of the templates to the polymers. The resulting figures of the dissociation constants and the corresponding binding site densities are displayed in Table 2 below.

TABLE 2

| Polymer | $K_D/M^{-1}$ | | $B_{max}/(\mu mol \cdot g^{-1})$ | |
|---|---|---|---|---|
| | High Affinity | Low Affinity | High Affinity | Low Affinity |
| MIP1 | $0.18 \cdot 10^{-6}$ | $1.59 \cdot 10^3$ | 0.21 | 280 |
| MIP3 | $1.23 \cdot 10^{-6}$ | $0.84 \cdot 10^{-3}$ | 0.37 | 130 |

These values are of the same order for the polymers, where the two-site model is somewhat more pronounced in the anti-cortisol polymer as reflected by a smaller number of sites with higher affinity and a larger density of sites with a lower affinity than the anti-corticosterone polymer. In comparison to natural antibodies these binding constants are lower, possibly resulting from the experimental conditions used. If a more sensitive assay method could be used, it would be feasible to measure the stronger binding affinities of the best sites.

The selectivities of the artificial antibodies were estimated from the measures of 50% displacement of radiolabelled template species from the polymers by non-radiolabelled displacing ligand ($IC_{50}$). The experimental design is analogous to standard competitive immunoassays used, where unlabelled ligands compete with the radio-labelled ligand for admission and binding to the sites. Dose-response curves obtained from experiments when unlabelled print species, cortisol or corticosterone, were used as competing ligands against MIP1 and MIP3 are displayed in FIGS. 10 and 11. The resulting values from the competition assays are presented in Table 3 together with the calculated cross-reactivities.

TABLE 3

| Ligand | anti-cortisol polymer | | anti-corticosterone polymer | |
|---|---|---|---|---|
| | $IC_{50}/\mu M$ | Cross-reactivity | $IC_{50}/\mu M$ | Cross-reactivity |
| Cortisol | 0.27 | 100 | 2.2 | 10 |
| Corticosterone | 3.1 | 8.5 | 0.22 | 100 |
| 21-Deoxycortisol | 6.7 | 4.0 | 41 | 0.54 |

TABLE 3-continued

| | anti-cortisol polymer | | anti-corticosterone polymer | |
|---|---|---|---|---|
| Ligand | $IC_{50}/\mu M$ | Cross-reactivity | $IC_{50}/\mu M$ | Cross-reactivity |
| 11-Deoxy-cortisol | 3.9 | 6.8 | 13 | 1.6 |
| Prednisolone | 0.74 | 36 | 3.8 | 5.7 |
| Cortisone | 30.0 | 0.89 | 57 | 0.38 |

From the structures of the various corticosteriods analyzed (FIGS. 2–7), the structural implications of the recognition can be deduced. For the anti-cortisol polymer (MIP1) the removal of one hydroxyl functionality of the imprinted structure leads to a decrease in binding as reflected by the increased $IC_{50}$-values. Removal of the 11-, 17-, or 21-OH groups, respectively, all reduce the binding by a factor of 11–25, where the 21-OH seems to be of higher importance for the recognition than the other hydroxyl groups. This can be viewed as the loss in hydrogen bonding between the hydroxyl groups of the corticosteroids and the carboxyl groups of the surrounding polymer will inevitably reduce the binding.

By introduction of an additional unsaturation in the structure in the Δ-1 position, prednisolone, the binding is not as severely affected. The cross-reactivity is as high as 36% compared to cortisol. This can be understood as a minor locking of the flexibility of the A-ring will not drastically affect the binding to the sites. A slight reduction in binding can be perceived since the prednisolone structure is unable to adapt to all of the configurations possible for cortisol.

On the other hand, changing the 11-OH group for a keto functionality as in cortisone, the binding is unprecendently reduced. One reason for this effect can be changes in hydrogen bonding capabilities of the cortisone as compared to the cortisol molecule. In the cortisol structure the hydroxyl group is able to act as both hydrogen donor and hydrogen acceptor, thereby stabilizing an interaction with the carboxyl functionality of the methacrylic acid residues of the polymer. The keto functionality of cortisone is unable to act as a hydrogen donor, leading to weaker interactions. Another explanation of this effect may be the sterical constraints of the cortisone structure in comparison to cortisol. The planar keto functionality, as opposed to the hydroxyl pointing in the β-position, may lead to changes in ring structure.

For the anti-corticosterone polymer (MIP3), introduction of an additional hydroxyl group in a 17-α-position (cortisol) reduces the binding to the polymer by a factor of 10. This is most probably due to stearic constraints of the cortisol molecule to fit into the more tightly formed site of corticosterone. Although further changes from the basic corticosterone structure of the other ligands studied, which differ from corticosterone in two positions, lead to higher selectivity of the anti-corticosterone polymer in comparison to the anti-cortisol polymer, the tendencies of the structural implications for the recognition can be seen.

Similarly, as with the case of the anti-cortisol polymer, removal of one hydroxyl functionality from the template species, reduces the binding to the sites by a factor of 6–19. Also very similar to the anti-cortisol polymer is the reduction in binding resulting from the introduction of a double bond in the A-ring (prednisolone), where the binding is reduced by 17%. The exchange of the 11-β-OH group for the planar keto group reduces binding by an additional 39%, much alike the binding by the anti-cortisol polymer.

In comparison to commercially used antibodies and antibodies reported in literature (Table 4), the artificial antibodies prepared by molecular imprinting exhibit strong similarities.

TABLE 4

| | Cross-reactivity (%) | | | | | |
|---|---|---|---|---|---|---|
| | Cortisol Assays | | | | Corticosterone Assays | |
| Ligand | ELISA[a] | RIA1[b] | RIA2[c] | RIA3[d] | RIA4[e] | RIA5[f] |
| Cortisol | 100 | 100 | 100 | 100 | 2.7 | 0.03 |
| Corticosterone | 10 | 1.0 | 0.6 | 3.0 | 100 | 100 |
| 21-Deoxy-cortisol | <0.1 | 8.0 | 0.3 | — | — | — |
| 11-Deoxy-cortisol | 19 | — | — | — | — | — |
| Prednisolone | 13 | 11 | 46 | — | — | — |
| Cortisone | — | — | — | 16 | — | — |

[a]Monoclonal mouse anti-cortisol antibodies [27]
[b]Sorin Biomedica, Almere, NL
[c]Diagnostic Products Corporation, Los Angeles, CA
[d]Polyclonal rabbit anti-cortisol serum [28]
[e]Polyclonal rat anti-corticosterone serum [29]
[f]ICN Biomedicals, Inc., Costa Mesa, CA The cross-reactivities of the anti-cortisol antibodies are roughly in the same order as those obtained by the anti-cortisol polymer. Normally, the naturally-raised antibodies are either subjected to some sort of screening process, or monoclonal, thus leading to an optimized performance. In the case of molecularly imprinted polymers, a range of binding sites are obtained, i.e., the polymers can be perceived as "polyclonal" in appearance. This fact will inevitably reduce the binding selectivities.

Figure 10:
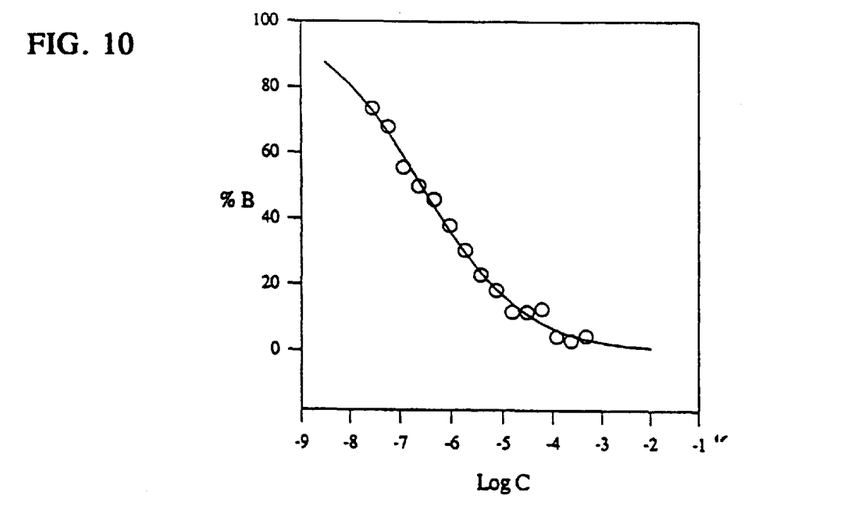
FIG. 10 shows the dose-response curves for the print species interactions with molecularly imprinted polymers, i.e., cortisol binding by anti-cortisol polymer MIP1, where B denotes the amount of bound radiolabelled ligand and C is the concentration of the competing ligand.
Figure 11:
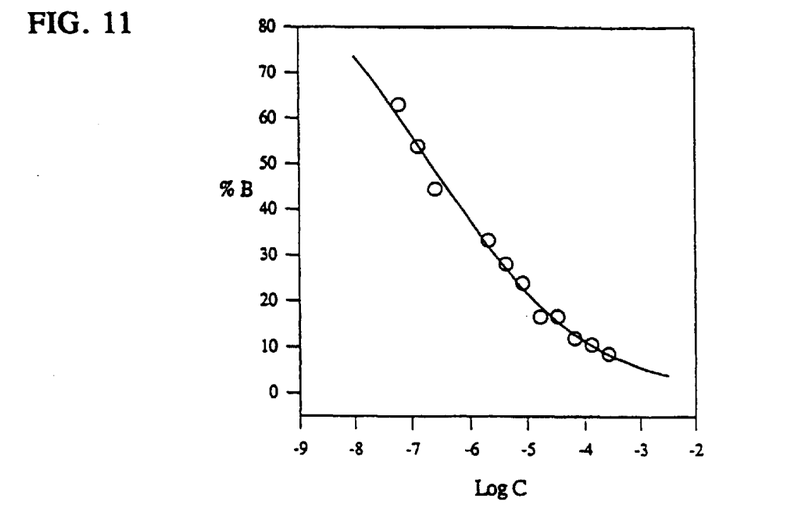
FIG. 11 shows the dose-response curves for the print species interactions with molecularly imprinted polymers, i.e., corticosterone binding by anti-corticosterone polymer (MIP3), where B denotes amount bound radiolabelled ligand and C is the concentration of the competing ligand.

The sensitivities of the assays using the artificial antibodies of the present invention, lie in the order of $10^{-7}$–$10^{-6}$M for cortisol and corticosterone using the anti-cortisol and anti-corticosterone polymers of the present invention, respectively, as indicated in the dose response curves displayed in FIGS. 10 and 11. This limitation is in part a consequence of the detection method used and may be further forced by finding a more sensitive analysis.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

REFERENCES

[1] H. Dugas, *Bioorganic Chemistry. A Chemical Approach To Enzyme Action,* 1989.
[2] D. R. Smith, Chem. Ind., *Supramolecular Chemistry,* 1994, pp. 14–17.
[3] K. Mosbach, et al., *The Emerging Technique Of Molecular Imprinting And Its Future Impact On Biotechnology,* Bio/Technology, 1996, 14, pp. 163–170.
[4] R. J. Ansell, et al., *Molecularly Imprinted Polymers For Bioanalysis: Chromatography, Binding Assays And Biomimetic Sensors,* Curr. Opin. Biotechnol., 1996, Vol. 7, pp. 89–94.
[5] G. Wulff, *Molecular Imprinting In Cross-Linked Materials With The Aid of Molecular Templates—A Way*

Towards Artificial Antibodies, Angew. Chem. Int. Ed. Engl., 1995, Vol. 34, pp. 1812–32.

[6] S. Vidyasankar, et al., Molecular Imprinting: Selective Materials For Separations, Sensors And Catalysis, Curr. Opin. Biotechnol., Vol. 6, pp. 218–224, 1995.

[7] K. J. Shea, Molecular Imprinting Of Synthetic Network Polymers: The De Novo Synthesis Of Macromolecular Binding And Catalytic Sites, Trends In Polymer Science, Vol. 2, pp. 166–173, 1994.

[8] L. Fischer, et al., Direct Enantioseparation of β-Adrenergic Blockers Using A Chiral Stationary Phase Prepared By Molecular Imprinting, J. Am. Chem. Soc., 1991, Vol. 113, pp. 9358–9360.

[9] M. Kempe, et al., Direct Resolution Of Naproxen On A Non-Covalently Molecularly Imprinted Chiral Stationary Phase, J. Chromatogr., 1994, Vol. 664, pp. 276–279.

[10] K. Nilsson, et al., Imprinted Polymers As Antibody Mimics And New Affinity Gels For Selective Separations In Capillary Electrophoresis, J. Chromatogr., 1994, Vol. 680, pp. 57–61.

[11] O. Ramstrom, et al., Synthetic Peptide Receptor Mimics: Highly Stereoselective Recognition In Non-Covalent Molecularly Imprinted Polymers, Tetrahedron: Asymmetry, 1994, Vol. 5, pp. 649–656.

[12] O. Ramstrom, et al., Chiral Recognition In Adrenergic Receptor Binding Mimics Prepared By Molecular Imprinting, J. Mol. Recogn., 1995, In Press.

[13] L. I. Andersson, et al., Mimics of The Binding Sites Of Opioid Receptors Obtained By Molecular Imprinting Of Enkephalin And Morphine, Proc. Natl. Acad. Sci., 1995, Vol. 92, pp. 4788–4792.

[14] L. I. Andersson, Development Of Aqueous Buffer And Organic Solvent Based Radioligand Binding Assays For (S)-Propranolol, Anal. Chem., 1996, Vol. 68, pp. 111–117.

[15] Kriz, et al., Introducing Biomimetic Sensors Based On Molecularly Imprinted Polymers As Recognition Elements, Anal. Chem., 1995, Vol. 67, pp. 2142–2144.

[16] G. Vlatakis, et al., Drug Assay Using Antibody Mimics Made By Molecular Imprinting, Nature, 1993, Vol. 361, pp. 645–647.

[17] S. E. Bystrom, et al., Selective Reduction Of Steroid 3- And 17-Ketones Using $LiAlH_4$ Activated Template Polymers, J. Am. Chem. Soc., 1993, Vol. 115, pp. 2081–2083.

[18] R. Muller, et al., Molecularly Imprinted Polymers Facilitating A β-Elimination Reaction, Makromol. Chem., Rapid Commun., 1993, Vol. 14, pp. 637–641.

[19] J. V. Beach, et al., Designed Catalysts. A Synthetic Network Polymer That Catalyzes The Dehydrofluorination Of 4-Fluoro-4-(p-nitrophenyl)butan-2-one, J. Am. Chem. Soc., 1994, Vol. 116, pp. 379–380.

[20] L. S. Goodman, et al., The Pharmacological Basis Of Therapeutics, Pergamon Press, Inc., 1990, 8th Ed.

[21] L. A. Kaplan, et al., Clinical Chemistry: Theory, Analysis And Correlation, C.V. Mosby Co., 1984.

[22] I. A. Nicholls, Thermodynamic Considerations For The Design Of And Ligand Recognition By Molecularly Imprinted Polymers, Chem. Lett., 1995, pp. 1035–1036.

[23] W. P. Jencks, On The Attribution And Additivity Of Binding Energies, Proc. Natl. Acad. Sci. USA, 1981, Vol. 78, pp. 4046–4050.

[24] M. Whitcombe, et al., A New Method For The Introduction Of Recognition Site Functionality Into Polymers Prepared By Molecular Imprinting: Synthesis And Characterization Of Polymeric Receptors For Cholesterol, J. Am. Chem. Soc., 1995, Vol. 117, pp. 7105–7111.

[25] K. Mosbach, et al., Preparation And Application Of Polymer-Entrapped Enzymes And Microorganisms In Microbial Transformation Process With Special Reference To Steroid 11-β-Hydroxylation And $\Delta^1$-Dehydrogenation, Biotech. Bioeng., 1970, Vol. 12, pp. 19–27

[26] S. B. Mahato, et al., Steroid Transformations By Microorganisms III, Phytochemistry, 1989, Vol. 1, pp. 7–40.

[27] Lewis, J. G., Manley, L., Whitlow, J. C. & Elder, P. A. 1992. Production of a monoclonal antibody to cortisol: application to a direct enzyme-linked immunosorbent assay of Plasma. Steroids 57, 82–85.

[28] Purchas, R. W., Zinn, S. A. & Tucker, H. A. 1985. A simple method for separating unbound and bound cortisol in a radioimmunoassay. Anal. Biochem. 149, 399–403.

[29] Sainio, E -L., Lehtola, T. & Roininen, P. (1988). Radioimmunoassay of total and free corticosterone in rat plasma: measurement of the effect of different doses of corticosterone. Steroids 51, 609–622.

We claim:

1. An artificial antibody, comprising:

non-covalently molecular imprinted copolymers having pre-determined, spatially positioned specific binding sites for a corticosteroid, wherein said copolymers are prepared by copolymerizing methacrylic acid with ethylene glycol dimethacrylate in the presence of a porogenic solvent and in the presence of a corticosteroid print molecule, wherein said porogenic solvent is tetrahydrofuran or acetone, and wherein said print molecule is cortisol or corticosterone.

2. The antibody according to claim 1, wherein said porogenic solvent is tetrahydrofuran.

3. The antibody according to claim 1, wherein said porogenic solvent is acetone.

4. The antibody according to claim 1, wherein said print molecule is cortisol.

5. The antibody according to claim 1, wherein said print molecule is corticosterone.

6. A method for producing an artificial polymeric antibody by non-covalent molecular imprinting, comprising:

i) combining methacrylic acid as a first monomer with corticosteroid print molecules in the presence of a porogenic solvent, wherein said print molecules are cortisol or corticosterone, and said porogenic solvent is tetrahydrofuran or acetone;

ii) adding ethylene glycol dimethacrylate as a crosslinking monomer to the methacrylic acid and print molecules of said step i);

iii) polymerizing said monomers to form a polymeric antibody by non-covalent molecular imprinting; and iv) removing the print molecules after step iii) to form an artificial polymeric antibody having predetermined spatially positioned, specific binding sites for corticosteroids.

7. The method according to claim 6, wherein said porogenic solvent is acetone.

8. The method according to claim 6, wherein said porogenic solvent is tetrahydrofuran.

9. The method according to claim 6, wherein said print molecules are cortisol.

10. The method according to claim 6, wherein said print molecules are corticosterone.

* * * * *